United States Patent [19]

Connor et al.

[11] 4,013,673
[45] Mar. 22, 1977

[54] 2,3-DIHYDRO-3-(2-PYRIDINYL)-4H-1-BENZOPYRAN-4-ONE N-OXIDES

[75] Inventors: David T. Connor, Parsippany; Patricia Young, Madison; Max Von Strandtmann, Rockaway, all of N.J.

[73] Assignee: Warner-Lambert Company, Morris Plains, N.J.

[22] Filed: Apr. 13, 1976

[21] Appl. No.: 676,441

[52] U.S. Cl. .................. 260/297 B; 260/296 B; 424/263; 260/297 R; 260/296 R
[51] Int. Cl.² .................................. C07D 405/04
[58] Field of Search ........ 260/297 B, 296 B, 345.2, 260/345.5

[56] References Cited
UNITED STATES PATENTS

| | | | |
|---|---|---|---|
| 2,621,189 | 12/1952 | Wiley | 260/345.2 |
| 3,419,560 | 12/1968 | Bernstein | 260/296 B |
| 3,704,323 | 11/1972 | Krapcho et al. | 260/296 B |

FOREIGN PATENTS OR APPLICATIONS

| | | | |
|---|---|---|---|
| 1,008,270 | 10/1965 | United Kingdom | 260/297 B |

*Primary Examiner*—Henry R. Jiles
*Assistant Examiner*—Robert T. Bond
*Attorney, Agent, or Firm*—Albert H. Graddis; Frank S. Chow

[57] ABSTRACT

There is disclosed 2,3-dihydro-3-(2-pyridinyl)-4H-1-benzopyran-4-one N-oxides of the formula:

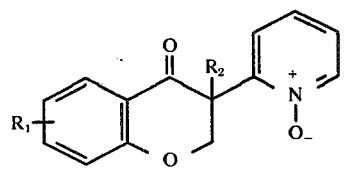

in which $R_1$ is hydrogen, halogen, lower alkyl, hydroxy, lower alkoxy or amino; $R_2$ is hydrogen or —CH$_2$OH. These compounds are indicated in the treatment of gastric ulcers.

5 Claims, No Drawings

2,3-DIHYDRO-3-(2-PYRIDINYL)-4H-1-BENZOPYRAN-4-ONE N-OXIDES

The present invention relates to 2,3-dihydro-3-(2-pyridinyl)-4H-1-benzopyran-4-one N-oxides having the following structural formula:

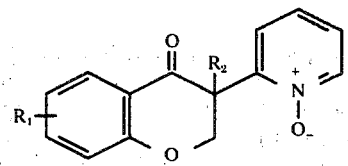

I in which $R_1$ is hydrogen, halogen, lower alkyl of 1–6 carbon atoms, lower alkoxy of 1–6 carbon atoms, hydroxy or amino; $R_2$ is hydrogen or —$CH_2OH$.

The present invention also includes within its scope a novel process for the production of the above compounds.

Included within the scope of the present invention are pharmaceutical dosage forms containing as active ingredients the aforesaid compounds.

The compounds of this invention, i.e., Compound I, exhibit gastric antiulcer activity. At a dose of 10–100 mg/kg in experimental animals such as rats, for example, when 2,3-dihydro-3-(2-pyridinyl)-4H-1-benzopyran-4-one N-oxide is tested according to the procedure described by H. Shay, et al., Gastroenterology, 5, 43 (1945), in the pylorus ligated rat, at a dose of 20 mg/kg intraperitoneally, it caused a reduction of 77.7% in volume of gastric acid and a 53.1% reduction in ion acid compared to controls. Thus, the compounds of this invention are indicated in the management of gastric hyperacidity or in the treatment of gastric ulcers. Generally, an oral or parenteral dose of 10–100 mg/kg, one to three times daily, is suggested to treat such conditions. This dosage regimen may be varied depending on the severity of the condition and the age and sex of the subject being treated.

The compounds of this invention are formulated into dosage forms such as tablets or capsules, using pharmaceutical diluents such as lactose, dicalcium phosphate and mannitol, by methods known in the pharmacist's art. The parenteral dosage forms are formulated by suspending the compounds of this invention in a parenterally acceptable vehicle such as water for injection and prepared into sterile dosage forms by methods well-known to the pharmacist's art.

According to the process of the present invention, Compound I is prepared by treating a compound of the formula:

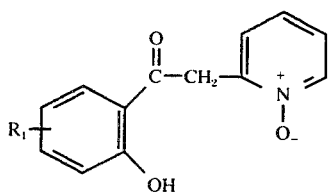

II with formaldehyde using an alcoholic solution of pyrrolidine as the solvent. The reaction temperature employed is the reflux temperature of the solvent employed, and the reaction is carried out under an atmosphere of nitrogen. When Compound II is treated with about an equivalent weight of formaldehyde, there is obtained those compounds of the invention in which $R_2$ is hydrogen. When an excess of formaldehyde is employed, there is obtained those compounds of this invention in which $R_2$ is —$CH_2OH$.

The reaction products thus obtained precipitate out of the reaction medium and are recovered by filtration techniques. Purification of the product is effected by techniques such as recrystallization from ethyl alcohol.

The starting Compound II is prepared in accordance with our teaching as set out in our co-pending application, Ser. No. 611,282, filed Sept. 5, 1975. The disclosure of said co-pending application is incorporated by reference herein.

Briefly, in order to prepare the starting Compound II above, a substituted benzoic acid ester of the formula III:

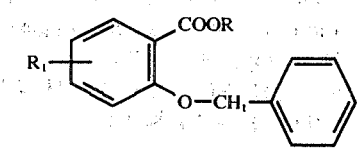

III wherein $R_1$ is hydrogen or lower alkyl and wherein R is lower alkyl is reacted with 2-picoline oxide of formula IV:

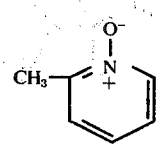

IV

The reaction is conducted in liquid ammonia, using an alkali metal condensing agent such as sodium, potassium or lithium amide. Sodium amide is preferred. This reaction produces an intermediate product of the formula V:

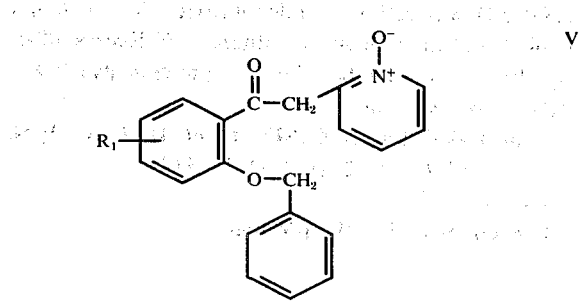

V wherein $R_1$ is hydrogen or lower alkyl.

Intermediate V is then subjected to catalytic reduction, using conventional methods. Typically, the reduction is conducted using gaseous hydrogen and a palladium-on-carbon catalyst. Ethyl acetate, acetic acid, or ethanol are suitable as solvents. The reaction proceeds most efficiently in acetic acid solution and is therefore preferred. Thus the reduction of the benzloxy substituent on intermediate compound V provides the corresponding hydroxy-substituted compounds of formula II, above.

To further illustrate the practice of this invention, the following examples are included:

EXAMPLE 1

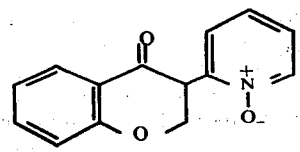

2,3-Dihydro-3-(2-pyridinyl)-4H-1-benzopyran-4-one N-oxide.

A mixture of 1-(2-hydroxyphenyl)-2-(2-pyridinyl)ethanone N-oxide (17.6 g, 0.076 mole) and 36% aqueous formaldehyde (5.85 g, 0.065 mole) in pyrrolidine (2ml) and methanol (200 ml) was refluxed under nitrogen for 5 hours, cooled, and the product was filtered off. Recrystallization from absolute ethanol gave white crystals (5.4 g, 28%), mp. 186°–187°.

Anal. Calcd. for $C_{14}H_{11}NO_3$: C, 69.70; H, 4.59; N, 5.80. Found: C, 69.64; H, 4.70; N, 5.84.

EXAMPLE 2

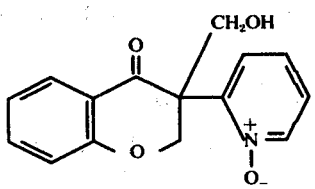

2,3-Dihydro-3-(hydroxymethyl)-3-(2-pyridinyl)-4H-1-benzopyran-4-one N-oxide.

A mixture of 1-(2-hydroxyphenyl)-2-(2-pyridinyl)ethanone N-oxide (30 g) and excess 36% aqueous formaldehyde (90 g) in pyrrolidine (3ml) and methanol (200 ml) was refluxed under nitrogen for 20 hours, cooled, and the product was filtered off. Recrystallization from absolute ethanol gave white crystals (28.8 g, 81%), mp. 184°–186°.

Anal. Calcd. for $C_{15}H_{13}NO_4$: C, 66.41; H, 4.83; N, 5.16. Found: C, 66.32; H, 4.94; N, 5.09.

We claim:
1. A compound of the formula:

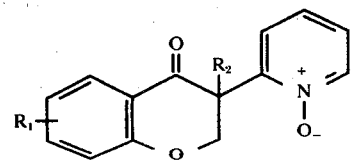

wherein $R_1$ is hydrogen, halogen, lower alkyl of 1–6 carbon atoms, hydroxy, lower alkoxy of 1–6 carbon atoms or amino and $R_2$ is hydrogen or —CH$_2$OH.

2. A compound according to claim 1 which is 2,3-dihydro-3-(2-pyridinyl)-4H-1-benzopyran-4-one N-oxide.

3. A compound according to claim 1 which is 2,3-dihydro-3-(hydroxymethyl)-3-(2-pyridinyl)-4H-1-benzopyran-4-one N-oxide.

4. A process for the production of a compound according to claim 1 in which $R_2$ is hydrogen which comprises refluxing together in an alcohol-pyrrolidine solvent, a compound of the formula:

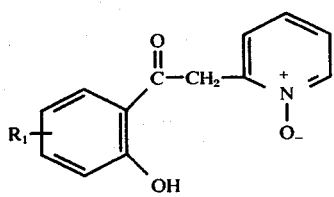

with about one equivalent of formaldehyde under an atmosphere of nitrogen.

5. A process for the production of a compound according to claim 1 in which $R_2$ is —CH$_2$OH, which comprises refluxing together in an alcohol-pyrrolidine solvent a compound of the formula:

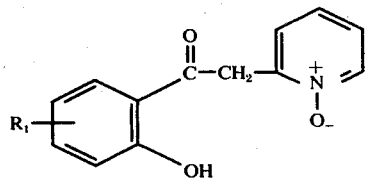

with an excess of formaldehyde under an atmosphere of nitrogen.

* * * * *